US011213553B2

(12) United States Patent
Majeed et al.

(10) Patent No.: US 11,213,553 B2
(45) Date of Patent: Jan. 4, 2022

(54) HYPOLIPIDEMIC EFFECTS OF BACILLUS COAGULANS

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN); Shaheen Majeed, Springville, UT (US)

(73) Assignee: SAMI LABS LIMITED, Bangalore (IN)

( * ) Notice: Subject to any disclaimer, the term of this patent is extended or adjusted under 35 U.S.C. 154(b) by 809 days.

(21) Appl. No.: 15/901,962

(22) Filed: Feb. 22, 2018

(65) Prior Publication Data
US 2018/0353553 A1 Dec. 13, 2018

Related U.S. Application Data

(60) Provisional application No. 62/517,320, filed on Jun. 9, 2017.

(51) Int. Cl.
| | |
|---|---|
| *A61K 39/00* | (2006.01) |
| *A61K 39/38* | (2006.01) |
| *A61K 39/07* | (2006.01) |
| *A01N 63/00* | (2020.01) |
| *A61K 35/742* | (2015.01) |
| *A61P 1/14* | (2006.01) |
| *A61K 9/00* | (2006.01) |
| *A61K 9/48* | (2006.01) |
| *A61K 9/20* | (2006.01) |
| *A23L 33/135* | (2016.01) |
| *A61K 35/00* | (2006.01) |

(52) U.S. Cl.
CPC .......... *A61K 35/742* (2013.01); *A23L 33/135* (2016.08); *A61K 9/0053* (2013.01); *A61K 9/0056* (2013.01); *A61K 9/2009* (2013.01); *A61K 9/2013* (2013.01); *A61K 9/2054* (2013.01); *A61K 9/4866* (2013.01); *A61P 1/14* (2018.01); *A23V 2002/00* (2013.01); *A61K 2035/115* (2013.01)

(58) Field of Classification Search
CPC .................................................. A61K 35/742
See application file for complete search history.

(56) References Cited

U.S. PATENT DOCUMENTS

| | | | | |
|---|---|---|---|---|
| 6,811,786 | B1* | 11/2004 | Farmer ................. | A23L 33/135 424/247.1 |
| 7,232,571 | B2 | 6/2007 | Farmer et al. | |
| 8,349,337 | B1 | 1/2013 | Farmer et al. | |
| 2005/0186189 | A1* | 8/2005 | Hsu ....................... | A61K 35/747 424/93.45 |
| 2006/0093591 | A1* | 5/2006 | Farmer ................. | A61K 31/445 424/93.45 |
| 2011/0236480 | A1* | 9/2011 | Ritter ..................... | A23L 33/21 424/466 |
| 2013/0195824 | A1* | 8/2013 | Farmer ................ | A61K 31/555 424/93.46 |

OTHER PUBLICATIONS

Sudha et al., International Journal of Probiotics and Prebiotics, 2011; 6(2):1-5 (Year: 2011).*
Panda et al., The Journal of Poultry Science, 2006; 43: 235-240 (Year: 2006).*
The Mayo Clinic, https://www.mayoclinic.org/diseases-conditions/high-blood-cholesterol/symptoms-causes/syc-20350800; Jul. 13, 2019 (Year: 2019).*
Majeed et al., J. Clin Toxicol, 2016; 6(1):5-9 (Year: 2016).*
Ataie-Jafari A, Larijani B, Alavi Majd H, Tahbaz F.Cholesterol-lowering effect of probiotic yogurt in comparison with ordinary yogurt in mildly to moderately hypercholesterolemic Subjects. Ann Nutr Metab.2009;54(1):22-7).
Ejtahed HS, Mohtadi-Nia J, Homayouni-Rad A, Niafar M, Asghari-Jafarabadi M, Mofid V, et al. Effects of probiotic yogurt containing Lactobacillus acidophilus and Bifidobacterium lactis on lipid profile in individuals with type 2 diabetes mellitus. J Dairy Sci. 2011;94(7):3288-94.
Chang BJ, Park SU, Jang YS, Ko SH, Joo NM, Kim SI, et al. Effect of functional yogurt NY-YP901 in improving the trait of metabolic syndrome. Eur J Clin Nutr. 2011;65(11):1250-5.
Xiao JZ, Kondo S, Takahashi N, Miyaji K, Oshida K, Hiramatsu A, et al. Effects of milk products fermented by Bifidobacterium longum on blood lipids in rats and healthy adult male volunteers. J Dairy Sci. 2003;86(7):2452-61.
Guo Z et al.," Influence of consumption of probiotics on the plasma lipid profile: a meta-analysis of randomised controlled trials", Nutr Metab Cardiovasc Dis. Nov. 2011;21(11):844-50. Jahreis G, Vogelsang H, Kiessling G, Schubert R, Bunte C, Hammes WP. Influence of probiotic sausage (*Lactobacillus paracasei*) on blood lipids and immunological parameters of healthy volunteers. Food Res Int. 2002; 35(2-3):133-8. [Consuming probiotic sausage containing 5×109 CFU of L. paracasei LTH 2579 for 5 weeks had no influence on serum lipids in hypercholesterolemic subjects].
Lewis SJ, Burmeister S. A double-blind placebo-controlled study of the effects of Lactobacillus acidophilus on plasma lipids. Eur J Clin Nutr. 2005; 59(6):776-80 [ Supplementing hypercholesterolemic patients with 6×1010 CFU of L. acidophilus for 6 weeks did not improve lipid profile in hypercholesterolemic subjects].

(Continued)

*Primary Examiner* — Gary B Nickol
*Assistant Examiner* — Lakia J Jackson-Tongue

(57) ABSTRACT

Disclosed is the hypolipidemic potential of *Bacillus coagulans*. More specifically the invention discloses the cholesterol lowering potential of *Bacillus coagulans* MTCC 5856 and therapeutic/biological indications thereof.

29 Claims, 2 Drawing Sheets

(56) References Cited

OTHER PUBLICATIONS

Simons LA, Amansec SG, Conway P. Effect of Lactobacillus fermentum on serum lipids in subjects with elevated serum cholesterol. Nutr Metab Cardiovasc Dis. 2006;16(8):531-5 [Probiotic capsules containing 4×109 CFU of L. fermentum for 10 weeks did not significantly modulate serum lipids in hypercholesterolemic subjects].

Hatakka K, Mutanen M, Holma R, Saxelin M, Korpela R, "Lactobacillus rhamnosus LC705 together with *Propionibacterium freudenreichii* ssp *shermanii* JS administered in capsules is ineffective in lowering serum lipids", J Am Coll Nutr. 2008; 27(4):441-7.

Elnaz Vaghef-Mehrabany et al., "Effects of probiotic supplementation on lipid profile of women with rheumatoid arthritis: A randomized placebo-controlled clinical trial", Health Promotion Perspectives, 2017, 7(2), 95-101 [Lactobacillus casei 1 could not improve serum lipids in rheumatoid arthritis patients].

Lye HS, Kuan CY, Ewe JA, Fung WY, Liong MT, The improvement of hypertension by probiotics: effects on cholesterol, diabetes, renin and phytoestrogens. Int J Dairy Sci. 2009;10(9):3755-75.

Ooi LG, Liong MT, "Cholesterol-lowering effects of probiotics and prebiotics: a review of in vivo and in vitro findings", Int J Mol Sci. 2010;11(6):2499-522].

Indian Council of Medical Research-Department of Biotechnology (ICMR-DBT), Guidelines for the evaluation of probiotics in food (2011), see section 2.3.

FAO/WHO Working Group Report on Drafting Guidelines for the Evaluation of Probiotics in Food London, Ontario, Canada, Apr. 30 and May 1, 2002.

\* cited by examiner

HYPOLIPIDEMIC EFFECTS OF *BACILLUS COAGULANS*

CROSS-REFERENCE TO RELATED PATENT APPLICATION

This application is non-provisional filing of U.S. provisional application No. 62/517,320 filed on 9 Jun. 2017, the content of which are incorporated herein by reference.

BACKGROUND OF THE INVENTION

Field of the Invention

The present invention in general relates to the therapeutic/biological effects of probiotic supplements. More specifically, the present invention relates to the hypolipidemic effect of *Bacillus coagulans*. Still more specifically, the present invention pertains to the cholesterol assimilation potential of *Bacillus coagulans* MTCC 5856 and therapeutic/biological indications thereof.

Description of Prior Art

The hypolipidemic effects of probiotic supplementation have been previously documented in the art as follows.
1. Ataie-Jafari A, Larijani B, Alavi Majd H, Tahbaz F. Cholesterol-lowering effect of probiotic yogurt in comparison with ordinary yogurt in mildly to moderately hypercholesterolemic Subjects. Ann Nutr Metab. 2009; 54(1):22-7.)
2. Ejtahed H S, Mohtadi-Nia J, Homayouni-Rad A, Niafar M, Asghari-Jafarabadi M, Mofid V, et al. Effects of probiotic yogurt containing *Lactobacillus acidophilus* and *Bifidobacterium lactis* on lipid profile in individuals with type 2 diabetes mellitus. J Dairy Sci. 2011; 94(7):3288-94.
3. Chang B J, Park S U, Jang Y S, Ko S H, Joo N M, Kim S I, et al. Effect of functional yogurt NY-YP901 in improving the trait of metabolic syndrome. Eur J Clin Nutr. 2011; 65(1):1250-5.
4. Xiao J Z, Kondo S, Takahashi N, Miyaji K, Oshida K, Hiramatsu A, et al. Effects of milk products fermented by *Bifidobacterium longum* on blood lipids in rats and healthy adult male volunteers. J Dairy Sci. 2003; 86(7): 2452-61.
5. Guo Z et al," Influence of consumption of probiotics on the plasma lipid profile: a meta-analysis of randomised controlled trials", Nutr Metab Cardiovasc Dis. 2011 November; 21(11):844-50.

U.S. Pat. Nos. 7,232,571, 8,349,337, 6,811,786 also disclose the cholesterol reducing property of *Bacillus coagulans* (Hammer strain) in combination with other cholesterol reducing agents and oligosaccharides. However, scientific literature also documents the inefficacy or poor efficacy of probiotic supplementation to exert hypocholesterolemic effects. Important ones include,
1. Jahreis G, Vogelsang H, Kiessling G, Schubert R, Bunte C, Hammes W P. Influence of probiotic sausage (*Lactobacillus paracasei*) on blood lipids and immunological parameters of healthy volunteers. Food Res Int. 2002; 35(2-3):133-8. [Consuming probiotic sausage containing $5 \times 10^9$ CFU of *L. paracasei* LTH 2579 for 5 weeks had no influence on serum lipids in hypercholesterolemic subjects]
2. Lewis S J, Burmeister S. A double-blind placebo-controlled study of the effects of *Lactobacillus acidophilus* on plasma lipids. Eur J Clin Nutr. 2005; 59(6):776-80 [Supplementing hypercholesterolemic patients with $6 \times 10^{10}$ CFU of *L. acidophilus* for 6 weeks did not improve lipid profile in hypercholesterolemic subjects].
3. Simons L A, Amansec S G, Conway P. Effect of *Lactobacillus fermentum* on serum lipids in subjects with elevated serum cholesterol. Nutr Metab Cardiovasc Dis. 2006; 16(8):531-5 [Probiotic capsules containing $4 \times 10^9$ CFU of *L. fermentum* for 10 weeks did not significantly modulate serum lipids in hypercholesterolemic subjects]
4. Hatakka K, Mutanen M, Holma R, Saxelin M, Korpela R, "*Lactobacillus rhamnosus* LC705 together with *Propionibacterium freudenreichii* ssp *shermanii* JS administered in capsules is ineffective in lowering serum lipids". J Am Coll Nutr. 2008; 27(4):441-7.
5. Elnaz Vaghef-Mehrabany et al, "Effects of probiotic supplementation on lipid profile of women with rheumatoid arthritis: A randomized placebo-controlled clinical trial", Health Promotion Perspectives, 2017, 7(2), 95-101 [*Lactobacillus casei* 1 could not improve serum lipids in rheumatoid arthritis patients].

While in general, the major mechanisms for hypolipidemic effects of probiotics include reduction of cholesterol absorption in the gut, enzymatic deconjugation of bile salts, incorporation of cholesterol into probiotic cell membranes, and conversion of cholesterol to coprostanol [Lye H S, Kuan C Y, Ewe J A, Fung W Y, Liong M T, "The improvement of hypertension by probiotics: effects on cholesterol, diabetes, renin and phytoestrogens. Int J Dairy Sci. 2009; 10(9):3755-75; and Ooi L G, Liong M T, "Cholesterol-lowering effects of probiotics and prebiotics: a review of in vivo and in vitro findings", Int J Mol Sci. 2010; 11(6):2499-5221, the inconsistent findings of hypocholesterolemic effects of probiotic microorganisms is a technical problem in the art. The technical solution to this problem lies in identifying a standalone strain-specific probiotic with lipid profile benefits much in line with the teachings that therapeutic benefits of probiotics is strain-specific and cannot be generalised. See, Indian Council of Medical Research-Department of Biotechnology (ICMR-DBT), "Guidelines for the evaluation of probiotics in food (2011), see section 2.3; and Joint FAO/WHO Working Group Report on Drafting Guidelines for the Evaluation of Probiotics in Food London, Ontario, Canada, April 30 and May 1, 2002, emphasising under Section 3.1 that "The current state of evidence suggests that probiotic effects are strain specific. Strain identity is important to link a strain to a specific health effect as well as to enable accurate surveillance and epidemiological studies".

It is thus the principle objective of the present invention to disclose the novel and non-obvious hypolipidemic effects of *Bacillus coagulans*.

It is yet another principle objective of the present invention to disclose the novel and non-obvious cholesterol assimilation effect of *Bacillus coagulans* MTCC 5856.

The present invention fulfils the aforesaid objectives and provides further related advantages.

SUMMARY OF THE INVENTION

The present invention discloses the hypocholesterolemic potential of *Bacillus coagulans* MTCC 5856 and therapeutic/biological indications thereof.

The advantages of the present invention include the identification of probiotic strain specific lipid profile benefits, in specific the novel and non-obvious hypocholesterolemic [cholesterol assimilation] effect of *Bacillus coagulans* MTCC 5856.

Other features and advantages of the present invention will become apparent from the following more detailed description, taken in conjunction with the accompanying images, which illustrate, by way of example, the principle of the invention.

DEPOSIT OF BIOLOGICAL MATERIAL

The deposit of biological material *Bacillus coagulans* SBC37-01 bearing accession number MTCC 5856, mentioned in the instant application has been made on 19 Sep. 2013 at Microbial Type Culture Collection & Gene Bank (MTCC), CSIR-Institute of Microbial Technology, Sector 39-A, Chandigarh—160036, India.

DETAILED DESCRIPTION OF THE MOST PREFERRED EMBODIMENTS

Figure 1:
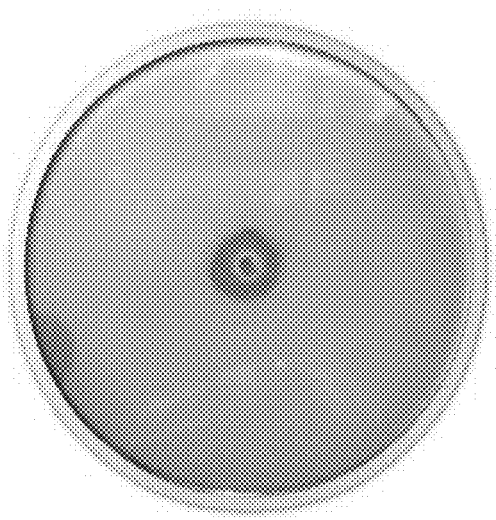
FIG. 1 shows Plate assay method for the Bile-Salt Hydrolase (BSH) activity determination using soft de Man Rogosa and Sharpe (MRS) agar supplemented with ox bile (0.3%, w/v) and $CaCO_3$ (0.1%, w/v). Hollow zone in the plate was the indication of bile salt hydrolase activity by the *Bacillus coagulans* MTCC 5856.

In the most preferred embodiment, the present invention relates to a method of cholesterol assimilation by probiotic bacteria *Bacillus coagulans*, said method comprising step of administering effective dose regimens of compositions containing said probiotic bacteria to mammals to bring about the effect of cholesterol reduction in the mammals. In a related embodiment, the *Bacillus coagulans* strain is *Bacillus coagulans* MTCC 5856. In another preferred embodiment, the *Bacillus coagulans* administered is a vegetative cell or spore. In yet another related embodiment, the spores include viable or heat killed or dead spores of *Bacillus coagulans*. In yet another related embodiment, the vegetative cells include viable or heat killed or dead cells of *Bacillus coagulans*. In another related embodiment, the *Bacillus coagulans* is administered orally in the form of tablets, capsules, syrups, gummies, powders, suspensions, emulsions, chewables, candies and eatables. In another related embodiment, the effective dose of *Bacillus coagulans* is about $1\times10^6$ to $1\times10^{14}$ colony forming units (CFU). In another related embodiment, the effective dose of *Bacillus coagulans* is preferably $2\times10^9$ cfu. In another related embodiment, the mammal is preferably human.

In another preferred embodiment, the present invention relates to a method of BSH production and bile salts deconjugation by using probiotic bacteria *Bacillus coagulans*, said method comprising step of administering effective dose regimens of compositions containing said probiotic bacteria to said mammals to bring about the desired effect of BSH production and bile salt deconjugation. In a related embodiment, production of BSH and deconjugating bile salts by the probiotic bacteria *Bacillus coagulans* results in effective cholesterol reduction in mammals. In a related embodiment, the *Bacillus coagulans* strain is *Bacillus coagulans* MTCC 5856. In another preferred embodiment, the *Bacillus coagulans* administered is a vegetative cell or spore. In yet another related embodiment, the spores include viable or heat killed or dead spores of *Bacillus coagulans*. In yet another related embodiment, the vegetative cells include viable or heat killed or dead cells of *Bacillus coagulans*. In another related embodiment, the *Bacillus coagulans* is administered orally in the form of tablets, capsules, syrups, gummies, powders, suspensions, emulsions, chewables, candies and eatables. In another related embodiment, the effective dose of *Bacillus coagulans* is about $1\times10^6$ to $1\times10^{14}$ cfu. In another related embodiment, the effective dose of *Bacillus coagulans* is preferably $2\times10^9$ cfu. In another related embodiment, the mammal is preferably human.

In yet another most preferred embodiment, the present invention relates to a method of preventing or treating hypercholesterolemia in mammals using probiotic bacteria *Bacillus coagulans*, said method comprising step of administering to said mammals effective dose regimens of compositions containing said probiotic bacteria to bring about the effect of lowering levels of circulating cholesterol in the blood of said mammals. In a related embodiment, the *Bacillus coagulans* strain is *Bacillus coagulans* MTCC 5856. In another preferred embodiment, the *Bacillus coagulans* administered is a vegetative cell or spore. In yet another related embodiment, the spores include viable or heat killed or dead spores of *Bacillus coagulans*. In yet another related embodiment, the vegetative cells include viable or heat killed or dead cells of *Bacillus coagulans*. In another related embodiment, the *Bacillus coagulans* is administered orally in the form of tablets, capsules, syrups, gummies, powders, suspensions, emulsions, chewables, candies and eatables. In another related embodiment, the effective dose of *Bacillus coagulans* is about $1\times10^6$ to $1\times10^{14}$ cfu. In another related embodiment, the effective dose of *Bacillus coagulans* is preferably $2\times10^9$ cfu. In another related embodiment, the mammal is preferably human.

In yet another most preferred embodiment, the present invention relates to a method of therapeutic management of dyslipidemia in mammals using probiotic bacteria *Bacillus coagulans*, said method comprising step of administering to said mammals effective dose regimens of compositions containing said probiotic bacteria to bring about the effect of lowering levels of circulating cholesterol in the blood, decreasing concentration of Low density lipoprotein (LDL), Low density lipoprotein (LDL)-cholesterol and lowering levels of circulating triglycerides in blood. In a related embodiment, the *Bacillus coagulans* strain is *Bacillus coagulans* MTCC 5856. In another preferred embodiment, the *Bacillus coagulans* administered is a vegetative cell or spore. In yet another related embodiment, the spores include viable or heat killed or dead spores of *Bacillus coagulans*. In yet another related embodiment, the vegetative cells include viable or heat killed or dead cells of *Bacillus coagulans*. In another related embodiment, the *Bacillus coagulans* is administered orally in the form of tablets, capsules, syrups, gummies, powders, suspensions, emulsions, chewables, candies and eatables. In another related embodiment, the effective dose of *Bacillus coagulans* is about $1\times10^6$ to $1\times10^{14}$ cfu. In another related embodiment, the effective dose of *Bacillus coagulans* is preferably 2×10⁹ cfu. In another related embodiment, the mammal is preferably human.

In yet another most preferred embodiment, therapeutic management of dyslipidemia is effected before the onset and for preventing disease conditions selected from the group consisting of high cholesterol induced atherosclerosis, coronary artery disease, hepatic steatosis and associated non alcoholic fatty liver disease, diabetes mellitus and obesity.

In another preferred embodiment, the invention discloses a method of reducing the cholesterol content in food stuff by probiotic bacteria *Bacillus coagulans*, said method comprising step of bringing into contact the prebiotic bacteria, together with bile salts and bile acids, with foods rich in cholesterol, to bring about the reduction and assimilation of cholesterol from the food stuff by the probiotic bacteria. In a related embodiment, the *Bacillus coagulans* strain is *Bacillus coagulans* MTCC 5856. In another related embodiment, foods rich in cholesterol is selected from the group consisting of, but not limited to, chicken liver, egg yolk, fish and fish oils, fast foods, animal fats and oil, seafood, processed meat, red meat, cheese, milk fat, butter and confectioneries.

The following illustrative examples are included to understand the technical features and advantages of the present invention.

Example 1: In-Vitro Estimation of Cholesterol Lowering Activity of *Bacillus coagulans* MTCC 5856

Methodology
Bile-Salt Hydrolase (BSH) Activity
a) Plate method: Plate assay method for BSH activity was performed as per the method described by the Dashkevicz M. P., Feighner S. D. (1989): Development of a differential medium for bile salt hydrolase-active *Lactobacillus* spp. Applied and Environmental Microbiology, 55: 11-16 and Ahn, Y T., G. B. Kim, K. S. Lim, Y. J. Baek, and H. U. Kim, "Deconjugation of bile salts by *Lactobacillus acidophilus* isolates," International Dairy Journal, vol. 13, no. 4, pp. 303-311, 2003 with minor modifications. Soft MRS agar was prepared by adding agar (1%, w/v) into MRS broth and then supplemented with bile salts (0.3% w/v; Ox Bile), and CaCO₃ (0.1%, w/v). This was autoclaved at 121° C. for 15 min and plates were prepared and dried at room temperature. *Bacillus coagulans* MTCC 5856 (10 µl corresponding to 2×10⁶ cfu/ml), which had been cultivated for 18 h, was inoculated on MRS agar by puncturing into the soft agar. Subsequently, plates were incubated at 37° C. for 72 h. Clearly visible halos around the punctures indicated the positive bile salt hydrolase (BSH) activity of the *Bacillus coagulans* MTCC 5856. Results were then assessed by measuring the diameters of halos. *Bacillus coagulans* MTCC 5856 grown on MRS agar without bile salts was used as the negative control. Measurements were repeated three times.
b) Thin Layer Chromatography (TLC) Method: Bile salt hydrolase activity of *Bacillus coagulans* MTCC 5856 was confirmed by following TLC plate method as described previously by the Guo C. F., Zhang I. W., Han X., Li J. Y., Du M., Yi H. X., Feng Z., Zhang Y. C., Xu X. R. (2011): Short communication: a sensitive method for qualitative screening of bile salt hydrolase-active lactobacilli based on thin-layer chromatography. Journal of Dairy Science, 94: 1732-1737. *Bacillus coagulans* MTCC 5856 was grown in MRS broth at 37° C. for 18 h, followed by centrifugation at 8000 rpm at 4° C. for 10 minutes. Cell pellets were then washed with 2 ml of sterile buffer (0.1 M PBS, pH 6.5). After washing, 5 ml of buffer solution was added to the cell pellets of *Bacillus coagulans* MTCC 5856. Bacterial suspension (1 ml) was mixed with reaction mix (1 ml). The reaction mix contained MRS broth, Sodium salt of taurodeoxycholate (TDC. 0.3% w/v) in phosphate buffer (0.1 mol/l), which gave a final pH of 6.5. The strains were then cultivated at 37° C. for 8 h. After the cultivation, the samples were vacuum evaporated and the residuals were subsequently dissolved in 1 ml of methanol, followed by centrifugation at 8,000 rpm for 5 minute. The supernatants were spotted onto the baselines on silica TLC plates (10×10 cm, TLC silica gel 60 F254; Merck) along with spotting of standard solutions, which were taurodeoxycholate in methanol (5 mmol/l), Deoxycholic acid in methanol (5 mmol/l). The mobile phase contained isoamyl acetate, propionic acid, n-propanol and water at a ratio of 40:30:20:10. The mobile phase was allowed to migrate along with TLC plates for 30 minutes. The plates were then dried and sprayed with 10% w/v solution of phosphomolybdic acid in ethanol, followed by drying at 80° C. for 5 min using hot air oven. Deoxycholic acid was liberated from bile salts by BSH positive *Bacillus coagulans* MTCC 5856. Results of TLC were evaluated by comparing with standards.

Bacterial Growth and Cholesterol Assimilation

Figure 3:
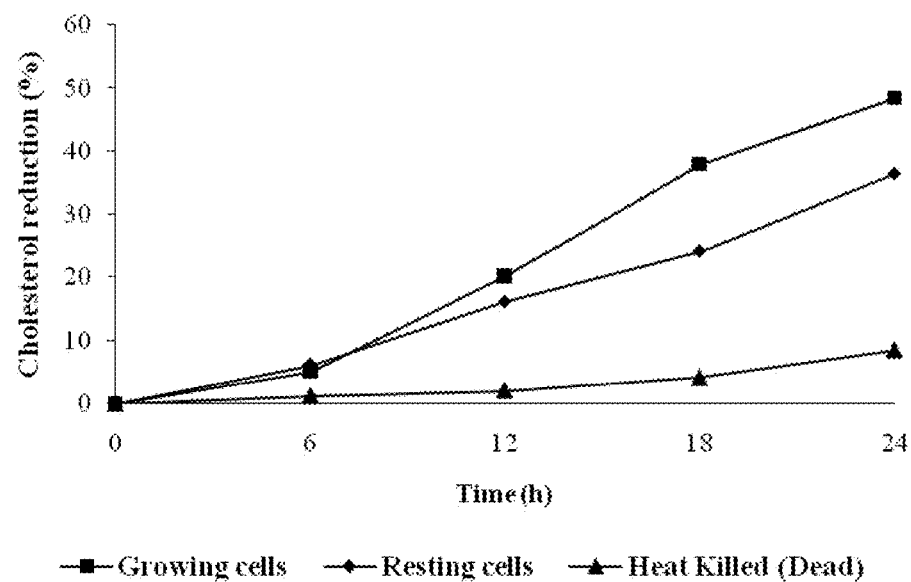
FIG. 3 shows the graphical representation of the effect of growing cells, resting cells and heat killed (dead) cells of the *Bacillus coagulans* MTCC 5856 on the cholesterol removal (%) as determined in the presence of ox bile (0.3%, w/v).

Growth of *Bacillus coagulans* MTCC 5856 in the presence of cholesterol was assessed at different time intervals till 24 h. *Bacillus coagulans* MTCC 5856 was inoculated in the sterilized MRS broth media supplemented with 0.30% ox-bile and 100 µg/ml water soluble cholesterol (polyoxyethanylcholesteryl sebacate). This was then incubated at 37° C. with gentle shaking (100 rpm) for 24 h. Samples were taken at different time intervals (0, 6, 12, 18 and 24 h) and the bacterial growth was measured at 600 nm using UV-spectrophotometer (Shimadzu UV-1601PC). Cholesterol assimilation determined according to the method described by the Rudel and Morris (1973) with some modifications proposed by Liong and Shah (2005). After the incubation, cells were centrifuged (8,000 rpm, at 4° C. for 10 min) and the remaining cholesterol concentration in the supernatant was determined using spectrophotometer (Shimadzu UV-1601PC) method. One ml of the aliquot was added with 1 ml of KOH (33% w/v) and 2 ml of absolute ethanol, vortexed for 1 min, followed by heating at 37° C. for 15 min. After cooling, 2 ml of distilled water and 3 ml of hexane were added and vortexed for 1 min. One ml of the hexane layer was transferred into a glass tube and evaporated. The residue was immediately dissolved in 2 ml of o-phthalaldehyde reagent. After complete mixing, 0.5 ml of concentrated sulfuric acid was added and the mixture was vortexed for 1 min. Absorbance was read at 550 nm after 10 min as described by Rudel L L, Morris M D. Determination of cholesterol using o-phthalaldehyde. *J Lipid Res*. 1973; 14 (3):364-6. All experiments were performed in triplicate and repeated twice. The cholesterol concentration was read off a standard curve prepared using the cholesterol stock solution (FIG. 3). The ability of *Bacillus coagulans* MTCC 5856 to assimilate cholesterol was expressed as the percentage of cholesterol removed at each incubation interval as follows:

Cholesterol assimilation/removal (%)=100−[(residual cholesterol after fermentation/Initial cholesterol added)×100].

Cholesterol Removal/Assimilation by Growing Cells, Resting Cells and Heat Killed (Dead) Cells of *Bacillus coagulans* MTCC 5856

The ability to assimilate/remove the cholesterol by the non-growing cells such as resting cells and heat killed (dead) cells of *Bacillus coagulans* MTCC 5856 was determined and compared with growing cells. Resting cells were prepared by growing *Bacillus coagulans* MTCC 5856 in MRS media overnight followed by centrifugation (8,000 rpm at 4° C. for 10 minutes) to obtained cell mass. This cell mass was further suspended into sterile phosphate buffer (0.05 M. pH 6.5) containing 0.3% (w/v) oxbile and 100 µg/ml of water-soluble cholesterol and then incubated for 24 h at 37° C. Heat killed (dead) cells were prepared by growing *Bacillus coagulans* MTCC 5856 in MRS media overnight followed autoclaving at 121° C. for 15 min. After autoclave, cells were collected by centrifugation (8,000 rpm at 4° C. for 10 minutes) and suspended aseptically in MRS broth supplemented with 0.3% (w/v) oxbile acid and 100 µg/ml of water-soluble cholesterol and then incubated for 24 h at 37° C. Growing cells were prepared by growing *Bacillus coagulans* MTCC 5856 in MRS media overnight and then 1 ml of this was added to the MRS broth supplemented with 0.3% (w/v) oxbile acid and 100 µg/ml of water-soluble cholesterol followed by incubation for 24 h at 37° C. After incubation, all the samples were centrifuged (8,000 rpm at 4° C. for 20 minutes) and cholesterol concentrations in the supernatants were measured following the Colorimetric method using Spectrophotometer as described above. All experiments were performed in triplicate and assayed twice.

Assimilation of Cholesterol from the Different Food Source by the *Bacillus coagulans* MTCC 5856 Under Gastric Stress The effect of cholesterol assimilation by the *Bacillus coagulans* MTCC 5856 on the cholesterol rich food source was investigated by the method described earlier by de Palencia P F, Lopez P, Corbi A L, Pelaez C, Requena T. Probiotic strains: survival under simulated gastrointestinal conditions, in vitro adhesion to Caco-2 cells and effect on cytokine secretion. Eur Food Res Technol 2008; 227: 1475-1484 and by Ritter P, Kohler C, von Ah U. Evaluation of the passage of *Lactobacillus gasseri* K7 and *Bifidobacteria* from the stomach to intestine using a single reactor model. BMC Microbiol 2009; 9: 87-95 with some modifications. A known weight of Egg yolk, butter (cow milk fat) and cleaned and processed chicken liver was taken in sterile beaker. Chicken liver was washed with the water and soaked into the 70% ethanol for 30 min and rinsed with sterile distilled water and then homogenized by adding into 0.2 M phosphate buffer pH 7.0. To mimic the in-vivo conditions, all samples were added to the 10 ml of a sterile electrolyte solution (6.2 g/L NaCl, 2.2 g/L KCl, 0.22 g/L $CaCl_2$ and 1.2 g/L $NaHCO_3$) and lysozyme (0.01%, Sigma-Aldrich) and pepsin (0.3%, Sigma-Aldrich). The pH of the samples was decreased to 1.5 by adding 1.0 mol/L HCl. *Bacillus coagulans* MTCC 5856 was added to each group and incubated at 37° C. with gentle shaking (100 rpm) for 3 h. After the incubation, pH of each sample was adjusted aseptically to 7.0 using sterile sodium bicarbonate saturated solution (8%, w/v). Oxygen reducing enzyme Oxyrase (Oxyrase® for Broth, Oxyrase Inc, Ohio, USA) was added to each flask to induce anaerobic environment. Sterile bile salt (0.3%, w/v, Sigma Aldrich) and pancreatin from porcine (0.1%, w/v, Sigma Aldrich) were also added to the each group. Sterile electrolyte solution containing 0.45% bile salts and 0.1% pancreatin (final concentration, both from Sigma Aldrich) were added to all the samples. All the samples were incubated at 37° C. with gentle shaking (100 rpm) for 24 h. After incubation, samples were centrifuged (8,000 rpm at 4° C. for 10 minutes) and cholesterol content was estimated in the supernatant by the method described above.

Results:

Bile Salt Hydrolase Activity of *Bacillus coagulans* MTCC 5856

*Bacillus coagulans* MTCC 5856 growth was observed on the agar plate containing ox bile and calcium carbonate which indicated its tolerance against ox bile and presence of bile salt hydrolase activity. There was 18 mm clear zone in the soft agar plate (FIG. 1) which indicated the presence of bile salt Hydrolase. Further, bile salt hydrolase activity was confirmed by TLC method which has more sensitivity and acceptability. The hydrolysis of sodium taurodeoxycholate and the formation of deoxycholic acid by the *Bacillus coagulans* MTCC 5856 clearly suggested the production of bile salt hydrolase. Rf value for standard deoxycholate was 0.89 which was matching with the Rf values of the deoxycholate liberated from the sodium taurodeoxycholate when incubated along with *Bacillus coagulans* MTCC 5856.

Figure 2:
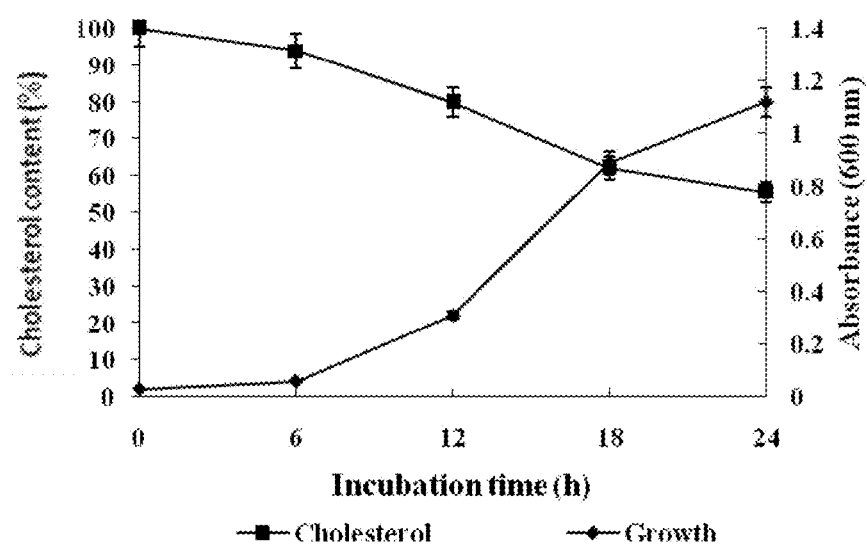
FIG. 2 shows the graphical representation of the effect of the *Bacillus coagulans* MTCC 5856 growth on the cholesterol reduction as determined in the presence of ox bile.

Assimilation/removal of cholesterol by the *Bacillus coagulans* MTCC 5856 There was a time dependant assimilation/removal of cholesterol by the *Bacillus coagulans* MTCC 5856 (FIG. 2). At 24 h of incubation, maximum removal of cholesterol was observed and also maximum growth was observed at 24 h. This indicated that the growth/colonization of *Bacillus coagulans* MTCC 5856 was responsible for the assimilation/removal of cholesterol. Further, different concentrations of cholesterol were added to media and incubated along with *Bacillus coagulans* MTCC 5856 for 24 h in presence of Ox bile (bile salt). Time dependent assimilation/removal of cholesterol was noticed (table 1). However, regardless of minimum concentration (25 µg/ml) or the maximum concentration (200 µg/ml) of cholesterol, the assimilation was almost similar and maximum assimilation/removal of cholesterol was noticed at 24 h of incubation (table 1).

TABLE 1

Effect of *Bacillus coagulans* MTCC 5856 on the reduction of cholesterol in the presence of ox bile.

| Time (h) | Cholesterol µg/ml, (%) | | | | | |
|---|---|---|---|---|---|---|
| 0 h | 25 ± 1.2 (100) | 50 ± 1.4 (100) | 75 ± 1.5 (100) | 100 ± 1.8 (100) | 150 ± 2.1 (100) | 200 ± 2.5 (100) |
| 6 h | 21.25 ± 1.1 (85.0) | 45.21 ± 1.2 (90.4) | 67.21 ± 1.6 (89.6) | 93.91 ± 1.9 (93.9) | 144.92 ± 1.9 (96.6) | 187.05 ± 1.9 (93.5) |
| 12 h | 13.4 ± 0.8 (53.6) | 37.12 ± 1.3 (74.2) | 48.15 ± 1.4 (64.2) | 79.92 ± 1.2 (79.9) | 119.15 ± 1.8 (79.43) | 156.11 ± 2.5 (78.0) |

TABLE 1-continued

Effect of *Bacillus coagulans* MTCC 5856 on the
reduction of cholesterol in the presence of ox bile.

| Time (h) | Cholesterol µg/ml, (%) | | | | | |
|---|---|---|---|---|---|---|
| 18 h | 12.14 ± 0.7 (48.5) | 30.25 ± 1.1 (60.5) | 36.15 ± 1.1 (48.2) | 62.1 ± 1.4 (62.1) | 93.1 ± 1.4 (62.0) | 95.1 ± 2.6 (47.5) |
| 24 h | 11.42 ± 0.8 (45.6) | 24.16 ± 0.7 (48.32) | 30.92 ± 1.3 (41.2) | 55.58 ± 1.1 (55.5) | 81.64 ± 1.8 (54.4) | 91.04 ± 1.8 (45.5) |

Assimilation/Removal of Cholesterol by the Non-Growing Cells of *Bacillus coagulans* MTCC 5856

The ability of *Bacillus coagulans* MTCC 5856, either growing or non-growing (resting or heat killed dead cells) to remove cholesterol was investigated. The removal of cholesterol varied remarkably in growing cells (48.42%) compared to resting and dead cells 36.46% and 8.5% in 24 h respectively (FIG. 3). However, resting cells and heat killed dead cells were also able to remove cholesterol. This indicated that the *Bacillus coagulans* MTCC 5856 has the ability to assimilate/remove the cholesterol in its growing or the non-growing form (resting and heat killed dead).

Figure 4:
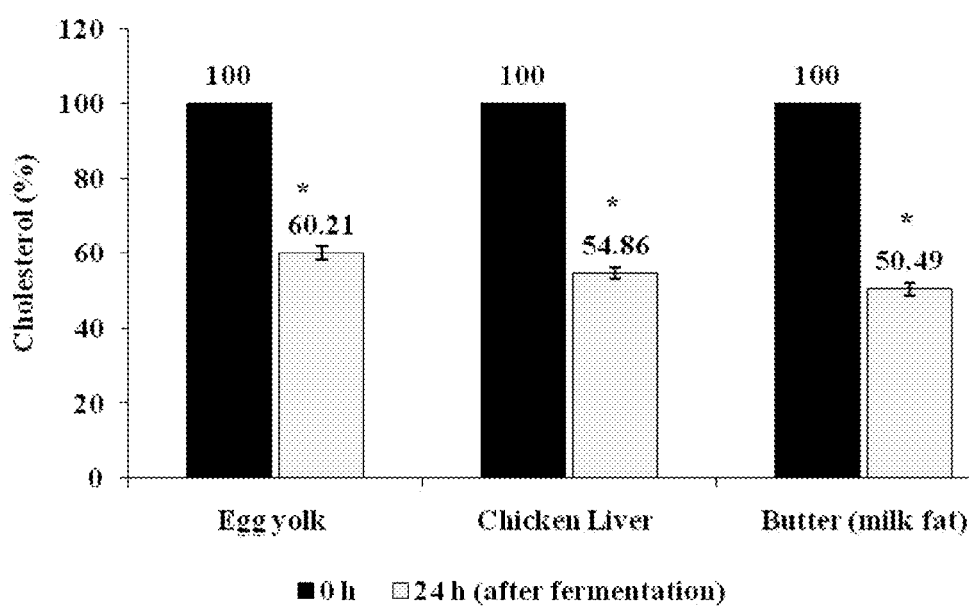
FIG. 4 shows the graphical representation of the effect of *Bacillus coagulans* MTCC 5856 on the assimilation/reduction of cholesterol from the different foods source (egg yolk, chicken liver and butter) was determined. $*p<0.05$; (Student's t test).

Assimilation/Removal of Cholesterol by *Bacillus coagulans* MTCC 5856 in Cholesterol Rich Foods The effect of *Bacillus coagulans* MTCC 5856 to assimilate/remove the cholesterol in cholesterol rich food source such as egg yolk, chicken liver and butter under gastric stress (acid and bile acids) was investigated with the aim to understand the in-vivo efficacy of *Bacillus coagulans* MTCC 5856. The significant reduction/assimilation of cholesterol was observed in all cholesterol rich food sources after 24 h of *Bacillus coagulans* MTCC 5856 fermentation (FIG. 4). The reduction of cholesterol in egg yolk, chicken liver and butter was 39.790%, 45.14% and 49.51% respectively after the 24 h of *Bacillus coagulans* MTCC 5856 fermentation. The data of the study concluded that *Bacillus coagulans* MTCC 5856 has the ability to assimilate/remove cholesterol in foods in an in-vivo mimicking conditions, thus, confirmed the efficacy.

Example 2: Hypolipidemic Effects of *Bacillus coagulans* MTCC 5856—a Clinical Evaluation Ethics
Institutional Ethics Committee All pertinent study documents were reviewed by the Institutional Ethics Committee (IEC), Life Care Hospital, Bangalore prior to study initiation and gave a favourable opinion. This IEC functions independently of Sami Labs Limited or ClinWorld Private Limited (CRO) and the operations are in compliance with Part 56 of Title 21 of the Code of Federal Regulations (CFR) and International Conference on Harmonization (ICH) guidelines. The aforementioned Ethics Committee was registered under CDSCO as per the Gazette Notification Number F.28-10/45-H(1), dated 21 Dec. 1945 and last amended vide notification number G. S. R. 76(E) dated 8 Feb. 2012.

Ethical Conduct of the Study

This research was conducted in accordance with the clinical research guidelines established by the Drugs and Cosmetics Act, 1940 of India, Drugs and Cosmetics Rules, 1945 of India, Ethical Guidelines for Biomedical Research on Human Participants, 2006 of Indian Council of Medical Research (ICMR) in India, the principles enunciated in the Declaration of Helsinki (Edinburgh, 2000) and the ICH—harmonized tripartite guideline regarding Good Clinical Practice (GCP).

Subject Information and Consent

Written and oral information about the study in a language easily understandable by the study volunteers was provided. Each volunteer was informed by the investigator, prior to the screening, of the purpose of this clinical trial, including possible risks and benefits and documented the informed consent process in the patient's file. Prior to entry into the study or initiation of any study related procedures, the patient read, signed and dated the IEC approved informed consent form. Sufficient time was provided for each subject to decide whether to participate in the study and all the questions and clarifications regarding the study were clarified by the investigator to the patient's satisfaction. The person executing the consent also signed and dated the final consent form page. The subject's willingness to participate in the study was documented in source notes by the Investigators. The original signed informed consent form has been summarized, in non-technical terms, the purpose of the study, the procedures to be carried out, and the potential hazards, if any.

Study Rationale

The current clinical study was planned to assess the efficacy and safety of *Bacillus coagulans* MTCC 5856 ($2\times10^9$ cfu) in patients with dyslipidemia (n=30).

Study Objectives
Primary Objective

The main objective was to assess the efficacy of *Bacillus coagulans* MTCC 5856 in Patients with dyslipidemia Efficacy Outcomes
Changes in Lipid Profile.
Change in quality of life.
Secondary Objective The secondary objective was to assess the safety of *Bacillus coagulans* MTCC 5856 ($2\times10^9$ cfu) in Patients with dyslipidemia.

Safety Outcomes
Any reports of adverse or serious adverse events.
Abnormal vital signs & lab parameters.
Selection of Study Population Subjects were included in the study if indicated "Yes" to all of the inclusion criteria and "No" to all of the exclusion criteria Inclusion Criteria The Inclusion Criteria were as follows:
1. Patients with dyslipidemia
2. Age between 30 and 65 years.
3. Have not consumed any probiotic for the last 2 months prior to recruitment.
4. Ability to comply with the study protocol.

Exclusion Criteria

The Exclusion Criteria were as follows:
1. Pregnant women, nursing mothers or subject who does not agree to assigned contraception in the study.
2. History of acute or chronic illness (such as cancer or arthritis rheumatoid).
3. Using any medication such as steroids or antibiotics which might affect viability of gut microorganism at recruitment and during intervention phase.
4. Participation in a clinical study during the preceding 90 days.
5. Any contraindication to blood sampling.
6. Patients using yogurt in their daily meal.

Treatment Line

Dose Administration and Treatment Regimen

Subjects were administered one capsule of *Bacillus coagulans* MTCC 5856 containing $2 \times 10^9$ cfu once a day orally for a period of 90 days.

Prior and Concomitant Therapy

History of any medications being used were elicited and documented. Any other medication that was used during the study duration was also documented. The subjects were followed up regularly and all concomitant dosing from the time of screening till the follow up visit was captured and recorded and co-morbid and concomitant medicine were captured in the study.

Treatment Compliance

Compliance with study medication was reviewed at each visit. The task was performed by examination of the returned medication and patient inquiry. All accountability records were incorporated into the investigator's study file.

Methodology for Assessment of Efficacy and Safety Variables

Changes in laboratory parameters from screening to day 90 were observed. Blood samples (12.0 ml) will be collected in centrifuge tubes at screening. Collection, sample shipment and processing will be performed as recommended or specified in the lab manual.

The Following was Assessed:

Hematology (Hemoglobin, Packed cell volume, White blood cell count-differential leukocyte count, Mean cell volume, Mean corpuscular hemoglobin, Mean corpuscular hemoglobin concentration, Mean platelet volume).

Complete lipid profile (Low density lipoprotein, Very low density lipoprotein, High density lipoprotein, Total Cholesterol, Triglycerides).

Urine Pregnancy test—All females who did not reach menopause will undergo a pregnancy test.

Statistical Methods

Laboratory data was summarized by presenting summary statistics of raw data and change from baseline values showing change from baseline to end of study. The statistical tools that was used and performed in this study will be detailed in the statistical analysis plan; the same will be followed for analysis. For continuous data such as age, the descriptive statistics Mean, Mode, Median, Q1, Q3, IQR, Whisker, 95% CI Mean and 95% CI was presented. For categorical data such as sex, the frequency and percentage was presented. For all the parameters like liver profile, anti-oxidant Enzymes (Biomarkers), Haematology, lipid Profile, and quality of life questionnaire were calculated from screening to visit 4. A p value was measured between screening and visit 4 over QOL domain. The p value was analyzed using Leven's scale Test on MINITAB. These scores were obtained using two sample t-test and multiple comparisons using method of null hypothesis over Levene's scale of mean change. The analysis of efficacy of the product was estimated on lipid and diabetic profile which was performed through ANOVA and multiple comparisons t-Test and method of null hypothesis. A mean P-Value change was observed and calculated for these efficacy parameters from Visit 1 to Visit 4 which was advised as Day 0 to Day 90 in the protocol. An average mean and P value was calculated with 95% CI mean for the safety parameters like Hematology profile from day 0 to Day 90 through t-test and ANOVA. For demographic profile average and range was obtained by simple statistical methods.

Safety Evaluations

The assessments for safety were based mainly on reporting of adverse events by the subjects. Other safety data (e.g., vital signs, laboratory tests) was summarized by presenting the number and no adverse events have occurred. Laboratory data was summarized by presenting summary statistics of raw data and change from screening values as well as shift tables showing changes from screening to end of study in laboratory values relative to normal reference limits.

Analysis of Adverse Events:

No adverse events were reported by the patients who turned up to the clinical site on Day 90 and until 15 days of telephonic follow-up.

Deaths, Other Serious Adverse Events, and Other Significant Adverse Events:

There were no Serious Adverse Events or Significant Adverse Events noticed in this study.

Results

Total 30 Subjects were enrolled observing a strict line on inclusion and exclusion criteria. Principal Investigator and study team strictly followed the protocol. The study's overall safety and efficacy parameters were calculated based on the mean value change and p value. The efficacy parameter of the study was estimated over lipid profile and the safety parameters were blood investigation like hematology and demographic profile. The results were justified with mean change between screening to Day 90 for the efficacy parameters. The below table reports the demographic data in the screening visit of the patients

TABLE 3

| Demographic data - Screening visit | | | | | | | | |
|---|---|---|---|---|---|---|---|---|
| Treatment Group: *Bacillus coagulans* MTCC 5856 | | | | | | | | |
| Parameter | Average | Median | Mode | Q1 | Q3 | Maximum | Minimum | Range |
| Age (years) | 51.83 | 51.5 | 46 | 46 | 60 | 65 | 33 | 65 |
| Weight (kg) | 66.5 | 65 | 72 | 61.25 | 71.75 | 93 | 36 | 93 |
| Height (cms) | 161.26 | 161.9 | 163 | 157.35 | 165.62 | 182.8 | 137.1 | 45.7 |
| BMI (kg/m$^2$) | 25.08 | 20.5 | 25.8 | 22.42 | 26.61 | 38.2 | 18.68 | 19.52 |
| Systolic Blood Pressure (mmHg) | 131.7 | 130 | 130 | 124 | 139.5 | 170 | 110 | 60 |

TABLE 3-continued

| Demographic data - Screening visit | | | | | | | |
|---|---|---|---|---|---|---|---|
| Diastolic Blood Pressure (mmHg) | 82.8 | 80 | 70 | 74.25 | 90 | 110 | 70 | 40 |
| Pulse Rate (b/min) | 74.16 | 71 | 71 | 71 | 77 | 90 | 71 | 19 |
| Heart Rate (b/min) | 71.8 | 71 | 71 | 71 | 72 | 74 | 71 | 3 |
| Respiration Rate (/min) | 20.8 | 21 | 21 | 21 | 21 | 22 | 19 | 22 |

| Gender & Diet | |
|---|---|
| Category | N (%) |
| Male | 21 (70%) |
| Female | 9 (30%) |
| Vegetarian | 13 (43.33%) |
| Non Vegetarian | 17 (56.67%) |

Q1: Quartile1 and
Q3: Quartile 3

Safety Evaluation

Extent of Exposure: 90 Days.

Brief summary of Adverse Event

For the safety evaluation the parameters considered in this study were physical examinations, vital signs namely blood Pressure, heart rate, Pulse rate and respiratory rate.

Analysis of Adverse Event

No statistically significant changes were observed with respect to vitals, laboratory parameters and clinical findings from screening to end of the study.

Listing of Individual Laboratory Measurements by the Patient and Each Abnormal Laboratory Value No abnormal laboratory values were observed.

Deaths, Other Serious Adverse Events and Other Significant Adverse Events

None of the patients enrolled in this study had any serious or significant adverse events. There were no deaths reported in this study.

Safety Conclusion

On the screening visit and during the whole course of the study the vital signs were normal. No statistical significant changes were observed. No clinically significance concerning safety was observed with respect to laboratory parameters from screening to end of the study.

The tables 4 and 5 report the safety parameters for the screening and final visit.

TABLE 4

| Safety Parameters (Hematology) for screening visit | | | | | | | | | | |
|---|---|---|---|---|---|---|---|---|---|---|
| | Mean | Mode | Median | Q1 | Q3 | IQR | Whisker | 95% CI Mean | 95% CI | P Value |
| Haemoglobin (g/dl) | 13.86 | 14.2 | 14.2 | 12.7 | 14.8 | 2.1 | 9.8, 16.9 | 14.2 | 13.05, 14.68 | 0.865 |
| Haematocrit (%) | 41.40 | 42.6 | 42.6 | 37.12 | 44.7 | 7.58 | 29.4, 50.7 | 42.6 | 38.62, 44.33 | 0.179 |
| RBC (million/mm$^3$) | 4.60 | 4.68 | 4.77 | 4.05 | 5.06 | 1.01 | 2.76, 5.86 | 4.77 | 4.18, 4.94 | 0.106 |
| Platelet Count (million/mm$^3$) | 2.32 | 2.09 | 2.4 | 2.09 | 2.65 | 0.56 | 1.32, 3.19 | 2.4 | 2.15, 2.55 | 0.677 |
| Leukocyte count (million/mm$^3$) | 7224.7 | 5900 | 7780 | 5820 | 8660 | 2840 | 3420, 10200 | 7780 | 5900, 8572.55 | 0.168 |
| Neutrophils (%) | 62.2 | 58 | 62 | 56.75 | 68 | 11.25 | 46, 80 | 62 | 58.23, 65.77 | 0.692 |
| Lymphocytes (%) | 33 | 38 | 34 | 27.5 | 39.25 | 11.75 | 16, 48 | 34 | 30, 38 | 0.476 |
| Monocytes (%) | 2.83 | 3 | 3 | 2 | 3 | 1 | 1, 4 | 3 | 2.23, 3 | 0.686 |
| Eosinophils (%) | 2.63 | 3 | 3 | 2 | 3 | 1 | 1, 3 | 3 | 2, 3 | 0.112 |
| Basophils (%) | 0 | 0 | 0 | 0 | 0 | 0 | 0 | 0 | 0 | 0 |
| MCV (fl) | 91.52 | 93.8 | 88.95 | 83.33 | 97.6 | 14.28 | 65.5, 116 | 88.9 | 84.214, 93.8 | 0.080 |
| MCH (pg) | 30.47 | 29.6 | 29.6 | 27.73 | 32.5 | 4.78 | 21.8, 38.6 | 29.6 | 28.05, 31.2 | 0.118 |
| MCHC (%) | 33.06 | 33.3 | 33.3 | 33 | 33.32 | 0.325 | 33, 33.7 | 33.3 | 33.1, 33.3 | 0.973 |
| MPV (fl) | 7.45 | 6.8 | 7.3 | 6.78 | 8.2 | 1.425 | 5, 9.2 | 7.3 | 6.8, 7.8 | 0.403 |

TABLE 5

Safety Parameters (Haematology) for final visit

| Parameter | Mean | Mode | Median | Q1 | Q3 | IQR | Whisker | 95% CI Mean | 95% CI | P Value |
|---|---|---|---|---|---|---|---|---|---|---|
| Haemoglobin (g/dl) | 14.09 | 13 | 14.05 | 12.88 | 15.4 | 2.52 | 9.3, 16.8 | 14.05 | 13.05, 15.18 | 0.0015 |
| Haematocrit (%) | 42.13 | 39 | 42.15 | 38.7 | 47.38 | 8.68 | 27.9, 54.6 | 42.15 | 39, 45.45 | 0.0087 |
| RBC (million/mm$^3$) | 4.94 | 4.63 | 4.90 | 4.59 | 5.5 | 0.91 | 3.59, 5.98 | 4.9 | 4.67, 5.09 | 0.0093 |
| Platelet Count (million/mm$^3$) | 2.19 | 2.42 | 2.18 | 1.68 | 2.66 | 0.97 | 0.91, 3.16 | 2.18 | 2.06, 2.42 | 0.00043 |
| Leukocyte count (million/mm$^3$) | 7433.33 | 6800 | 7500 | 6425 | 8725 | 2300 | 3100, 10200 | 7500 | 6800, 8377.13 | 0.0027 |
| Neutrophils (%) | 61.5 | 63 | 63 | 58 | 67.25 | 9.25 | 45, 72 | 63 | 61, 64 | 2.96 |
| Lymphocytes (%) | 32.66 | 29 | 30.5 | 28 | 36 | 8 | 24, 48 | 30.5 | 29, 34 | 1.61 |
| Monocytes (%) | 3.93 | 5 | 4 | 2.75 | 5 | 2.25 | 2, 7 | 4 | 3, 5 | 0.00014 |
| Eosinophils (%) | 1.9 | 2 | 2 | 2 | 2 | 0 | 1, 3 | 2 | 2, 2 | 6.94 |
| Basophils (%) | 0 | 0 | 0 | 0 | 0 | 0 | 0 | 0 | 0 | 0 |
| MCV (fl) | 85.74 | 87 | 84.7 | 79.75 | 89.03 | 9.27 | 66.6, 102.5 | 84.7 | 82.05, 87 | 4.48 |
| MCH (pg) | 28.62 | 28.6 | 28.45 | 26.52 | 89.65 | 3.125 | 22.3, 34.1 | 28.45 | 27.25, 28.95 | 6.72 |
| MCHC (%) | 33.63 | 33.3 | 33.3 | 33.1 | 33.62 | 0.525 | 32.9, 33.8 | 33.3 | 33.2, 33.48 | 1.59 |
| MPV (fl) | 7.62 | 7.9 | 7.55 | 6.9 | 8 | 1.1 | 6.2, 8.9 | 7.55 | 7.22, 7.9 | 1.76 |

Efficacy Evaluation

For efficacy parameters like total cholesterol. LDL, TG and quality of life the mean p value change for *Bacillus coagulans* MTCC 5856 was obtained as p≤0.05 which means *Bacillus coagulans* MTCC 5856 had showed statistical significant effect on total cholesterol, LDL, TG and quality of life from day 0 to day 90.

TABLE 6

Mean change in Lipid Profile

| | *Bacillus coagulans* MTCC 5856 | |
|---|---|---|
| Visits | Mean ± SD | p value Between the visits |
| Triglycerides (mg/dL) | | |
| Baseline (Day 0) | 209.2 ± 107.2 | p < 0.05 |
| Final Visit (Day 90) | 191.1 ± 110.3 | |
| Total Cholesterol (mg/dL) | | |
| Baseline (Day 0) | 264.4 ± 34.1 | p < 0.05 |
| Final Visit (Day 90) | 220.4 ± 37.9 | |
| LDL (mg/dL) | | |
| Baseline (Day 0) | 166.2 ± 46.4 | p < 0.05 |
| Final Visit (Day 90) | 129.1 ± 47.2 | |
| HDL (mg/dl) | | |
| Baseline (Day 0) | 50.48 ± 6.56 | p > 0.05 |
| Final Visit (Day 90) | 52.31 ± 10.80 | |
| VLDL (mg/dl) | | |
| Baseline (Day 0) | 37.32 ± 17.32 | p > 0.05 |
| Final Visit (Day 90) | 33.31 ± 14.62 | |

Example 3: Cholesterol Lowering Compositions/Formulations Containing *Bacillus coagulans*

Tables 7, 8 and 9 provide illustrative examples of food formulations containing *Bacillus coagulans* for lowering cholesterol.

TABLE 7

NutriCereal Premix (Vanilla Flavour)

Active Ingredients

*Bacillus coagulans* MTCC 5856 ($1 \times 10^6$ to $1 \times 10^{14}$ cfu), Inulin, Fabenol ® Max (*Phaseolus vulgaris* extract)

Excipients

Corn Flakes (Crushed to 4 mm), Skimmed Milk Powder, Soya Protein Isolate, Carageenan, Sucralose, Vanilla Flavour Note:
® Registered Trademark of Sabinsa Corporation, USA

TABLE 8

NutriCereal Premix (Strawberry Flavour)

Active Ingredients

*Bacillus coagulans* MTCC 5856 ($1 \times 10^6$ to $1 \times 10^{14}$ cfu), Inulin, Fabenol ® Max (*Phaseolus vulgaris* extract)

Excipients

Corn Flakes (Crushed to 4 mm), Skimmed Milk Powder, Soya Protein Isolate, Carageenan, Sucralose, Strawberry Flavour, Sabeet ® (Beetroot extract)

Note:
® Registered Trademark of Sabinsa Corporation, USA

TABLE 9

Instant Dairy Dessert Premix

| Active Ingredients |
| --- |
| Bacillus coagulans MTCC 5856 ($1 \times 10^6$ to $1 \times 10^{14}$ cfu), Fructo Oligosachharides |
| Excipients |
| Starch (N Creamer 180), Skimmed Milk Powder, Pectin, Whole milk powder, Sucralose, Citric Acid, Malic Acid, Salt, Yogurt flavour, Vannila Flavour, Tri sodium citrate, Guar gum |

Tables 10, 11 and 12 provide illustrative examples of nutraceutical formulations containing *Bacillus coagulans* for lowering cholesterol.

TABLE 10

Bacillus coagulans Chewable Tablet (For Cholesterol Lowering)

| Active Ingredients |
| --- |
| Bacillus coagulans MTCC 5856<br>1 billion cfu |
| Excipients |
| Sugar, Flavouring agent (Vanilla ice cream Flavour), Magnesium stearate |

Note:
*Bacillus coagulans* has total viable count of 15 billion spores per gram.

TABLE 11

Bacillus coagulans Tablet (For Cholesterol Lowering)

| Active Ingredients |
| --- |
| Bacillus coagulans MTCC 5856<br>2 billion cfn |
| Excipients |
| Microcrystalline cellulose, Colloidal silicon dioxide, Magnesium stearate |

Note:
*Bacillus coagulans* has total viable count of 15 billion spores per gram.

TABLE 12

Bacillus coagulans Capsule (For Cholesterol Lowering)

| Active Ingredients |
| --- |
| Bacillus coagulans MTCC 5856<br>2 billion cfu |
| Excipients |
| Microcrystalline cellulose |

Note:
*Bacillus coagulans* has total viable count of 15 billion spores per gram.

The above formulations are just illustrative examples, any formulation containing the above active ingredient intended for the said purpose will be considered equivalent.

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A method of managing hypercholesterolemia in mammals by cholesterol assimilation, absorption and removal by probiotic bacteria *Bacillus coagulans* MTCC 5856, said method comprising the step of administering to said mammals effective dose regimens of compositions containing said probiotic bacteria, to bring about the effect of cholesterol removal/reduction in mammals by said bacteria.

2. The method as in claim 1, wherein the *Bacillus coagulans* is administered in the form of vegetative cell or spore.

3. The method as in claim 1, wherein the *Bacillus coagulans* is administered orally in the form of tablets, capsules, syrups, gummies, powders, suspensions, emulsions, chewables, candies and eatables.

4. The method as in claim 1, wherein the effective dose of *Bacillus coagulans* is about $1 \times 10^6$ to $1 \times 10^{14}$ cfu.

5. The method as in claim 1, wherein the effective dose of *Bacillus coagulans* is preferably $2 \times 10^9$ cfu.

6. The method as in claim 1, wherein the mammal is preferably human.

7. A method of managing hypercholesterolemia in mammals by increasing bile salt hydrolase production and bile salts deconjugation by probiotic bacteria *Bacillus coagulans* MTCC 5856, said method comprising the step of administering effective dose regimens of compositions containing said probiotic bacteria to said mammals to bring about the desired effect of bile salt hydrolase production and bile salt deconjugation.

8. The method as in claim 7, wherein production of BSH and deconjugating bile salts by the probiotic bacteria *Bacillus coagulans* results in effective cholesterol reduction in mammals.

9. The method as in claim 7, wherein the *Bacillus coagulans* administered is a vegetative cell or spore.

10. The method as in claim 7, wherein the *Bacillus coagulans* is administered orally in the form of tablets, capsules, syrups, gummies, powders, suspensions, emulsions, chewable, candies and eatables.

11. The method as in claim 7, wherein the effective dose of *Bacillus coagulans* is about $1 \times 10^6$ to $1 \times 10^{14}$ cfu.

12. The method as in claim 7, wherein the effective dose of *Bacillus coagulans* is preferably $2 \times 10^9$ cfu.

13. The method as in claim 7, wherein the mammal is preferably human.

14. A method of treating hypercholesterolemia in mammals using probiotic bacteria *Bacillus coagulans* MTCC 5856, said method comprising the step of administering in said mammals effective dose regimens of compositions containing said probiotic bacteria to bring about the effect of lowering levels of circulating cholesterol in the blood of said mammals.

15. The method as in claim 14, wherein the *Bacillus coagulans* is administered in the form of vegetative cell or spore.

16. The method as in claim 14, wherein the *Bacillus coagulans* is administered orally in the form of tablets, capsules, syrups, gummies, powders, suspensions, emulsions, chewable, candies and eatables.

17. The method as in claim 14, wherein the effective dose of *Bacillus coagulans* is about $1 \times 10^6$ to $1 \times 10^{14}$ cfu.

18. The method as in claim 14, wherein the effective dose of *Bacillus coagulans* is preferably $2 \times 10^9$ cfu.

19. The method as in claim 14, wherein the mammal is preferably human.

20. A method of therapeutic management of dyslipidemia in mammals using probiotic bacteria *Bacillus coagulans*, said method comprising step of administering to said mammals effective dose regimens of compositions containing said probiotic bacteria to bring about the effect of lowering levels of circulating cholesterol in the blood, decreasing concentration of Low density lipoprotein, Low density lipoprotein-cholesterol and lowering levels of circulating triglycerides in blood.

21. The method as in claim 20, wherein the *Bacillus coagulans* strain is *Bacillus coagulans* MTCC 5856.

22. The method as in claim 20, wherein the *Bacillus coagulans* is administered in the form of vegetative cell or spore.

23. The method as in claim 20, wherein the spores include viable or heat killed or dead spores of *Bacillus coagulans*.

24. The method as in claim 20, wherein the vegetative cells include viable or heat killed or dead cells of *Bacillus coagulans*.

25. The method as in claim 20, wherein the *Bacillus coagulans* is administered orally in the form of tablets, capsules, syrups, gummies, powders, suspensions, emulsions, chewable, candies and eatables.

26. The method as in claim 20, wherein the effective dose of *Bacillus coagulans* is about $1 \times 10^6$ to $1 \times 10^{14}$ cfu.

27. The method as in claim 20, wherein the effective dose of *Bacillus coagulans* is preferably $2 \times 10^9$ cfu.

28. The method as in claim 20, wherein therapeutic management of dyslipidemia is effected before the onset of disease conditions selected from the group consisting of high cholesterol induced atherosclerosis, coronary artery disease, hepatic steatosis and associated non-alcoholic fatty liver disease, diabetes mellitus and obesity.

29. The method as in claim 20, wherein the mammal is preferably human.

* * * * *